United States Patent [19]

Zinnen

[11] Patent Number: 4,784,807
[45] Date of Patent: Nov. 15, 1988

[54] PROCESS FOR SEPARATING TRIGLYLCERIDES BY DEGREE OF UNSATURATION

[75] Inventor: Hermann A. Zinnen, Evanston, Ill.

[73] Assignee: UOP Inc., Des Plaines, Ill.

[21] Appl. No.: 70,266

[22] Filed: Jul. 6, 1987

[51] Int. Cl.$^4$ .............................................. C11B 3/00
[52] U.S. Cl. .............................. 260/405.5; 260/428; 260/428.5
[58] Field of Search ................. 260/405.5, 428, 428.5, 260/410.7

[56] References Cited

U.S. PATENT DOCUMENTS

4,048,205  9/1977  Neuzil et al. ................... 260/428
4,353,838 10/1982  Cleary et al. .................. 260/419

Primary Examiner—Werren B. Lone
Assistant Examiner—Vera C. Clarke
Attorney, Agent, or Firm—Thomas K. McBride; John F. Spears, Jr.; Jack H. Hall

[57] ABSTRACT

The separation of polyunsaturated triglycerides from monounsaturated triglycerides is performed by an adsortive chromatographic process in liquid phase using hydrogen-, copper-, or potassium-exchanged omega zeollites or carbon as the adsorbent. A ketone, toluene or ketone/n-aliphatic hydrocarbon can be selected as the desorbent.

17 Claims, 5 Drawing Sheets

PROCESS FOR SEPARATING TRIGLYLCERIDES BY DEGREE OF UNSATURATION

FIELD OF THE INVENTION

The field of art to which this invention belongs is the solid bed adsorptive separation of glycerides. More specifically, the invention relates to a process for separating triglycerides from triglycerides on the basis of degree of unsaturation by a process which employs Cu, H, or K-exchanged omega zeolites.

BACKGROUND OF THE INVENTION

The separation of many classes of compounds by selective adsorption on molecular sieves or zeolites as well as other adsorbents is well known. For example, as disclosed in U.S. Pat. No. 4,048,205, methyl esters of fatty acids of various degrees of unsaturation may be separated from mixtures of esters of saturated and unsaturated fatty acids with X or Y zeolites exchanged with a selected cation. Further, in U.S. Pat. No. 4,353,838 it is disclosed that monoethanoid fatty acids may be separated from diethanoid fatty acids with cross-linked polystyrenes, e.g. "Amberlite".

The process of separating triglycerides described herein has many potential uses, for example, the fractionation of triglycerides, e.g., palm olein. Also oils, such as soybean oil, can be processed to give fractions which are enriched or depleted in unsaturation.

Another important application of my separation process resides in its utility in triglyceride synthesis. Cocoa butter, for example, is a high value natural product consisting predominantly of a mixture of particular triglycerides where the 2-position of glycerol is esterified with an oleyl group and the 1- and 3-positions are esterified with either the palmitoyl or the stearyl group. Both the palmitoyl and stearyl groups are fully saturated, i.e., no double bond unsaturation exists on either groups' hydrocarbon chain. However, the oleyl group is unsaturated to provide the glycerides with a single site of unsaturation. The cocoa butter being primarily monounsaturated has been referred to as a monounsaturated triglyceride (MUT). Cocoa butter is a predominant component in chocolate confections. It is believed that large quantities of triglycerides could be synthesized and used as cocoa butter extenders by reaction of free fatty acids with glycerol or by selective hydrogenation of polyunsaturated triglycerides, followed by separation of the resulting mixtures by degree of unsaturation.

I have discovered combinations of zeolites, carbons and desorbents which separate the triglycerides based on differences in unsaturation. The triglycerides which are adsorbed preferentially to other triglycerides are concentrated in the extract. The other triglycerides, therefore, are removed from the mixture of triglycerides and are concentrated in the raffinate of the adsorptive separation apparatus.

SUMMARY OF THIS INVENTION

The present invention is a process for separating triglycerides from a feed mixture comprising at least two triglycerides having different degrees of unsaturation or saturation. The process comprises contacting the mixture at adsorption conditions with an adsorbent comprising an omega type zeolite exchanged with copper, hydrogen ion, or potassium or an activated carbon or carbonized polymeric resin. With the omega zeolite, the triglyceride, which is more unsaturated, is selectively adsorbed in preference to the more saturated triglycerides. Using a carbon as adsorbent, the less unsaturated triglycerides, e.g., monounsaturated triglycerides (MUT), are adsorbed in preference to the more unsaturated triglycerides, e.g., polyunsaturated triglycerides (PUT). Next, the adsorbed triglyceride is desorbed by a liquid ketone, toluene or a mixture of a ketone and paraffin desorbents. The desorbent may be selected from the ketones having up to 7 carbons, e.g., acetone, the pentanones, hexanones and heptanones. Specific examples of desorbent liquids useful in the process are toluene, acetone, methylethyl ketone, diethyl ketone, methylpropyl ketone, 2-hexanone, 2-heptanone, etc. and mixtures thereof with hexane.

The steps of the process are: (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone defined by the adsorbent located between a feed input stream at an upstream boundary of the zone and a raffinate output stream at a downstream boundary of the zone; (c) maintaining a purification zone immediately upstream from the adsorption zone, the purification zone defined by the adsorbent located between an extract output stream at an upstream boundary of the purification zone and the feed input stream at a downstream boundary of the purification zone; (d) maintaining a desorption zone immediately upstream from the purification zone, the desorption zone defined by the adsorbent located between a desorbent input stream at an upstream boundary of the zone and the extract output stream at a downstream boundary of the zone; (e) passing the feed mixture into the adsorption zone at adsorption conditions to effect the selective adsorption of the more saturated triglycerides by the adsorbent in the adsorption zone and withdrawing a raffinate output stream from the adsorption zone; (f) passing a desorbent material into the desorption zone at desorption conditions to effect the displacement of the adsorbed triglycerides from the adsorbent in the desorption zone; (g) withdrawing an extract output stream comprising less saturated triglycerides and desorbent material from the desorption zone; (h) withdrawing a raffinate output stream comprising triglycerides from the desorption zone; (i) periodically advancing through the column of adsorbent in a downstream direction with respect to fluid flow in the adsorption zone, the feed input stream, raffinate output stream, desorbent input stream, and extract output stream to effect the shifting of zones through the adsorbent and the production of extract output and raffinate output streams.

Other embodiments of our invention encompass details about feed mixtures, adsorbents, desorbent materials and operating conditions all of which are hereinafter disclosed in the following discussion of each of the facets of the present invention.

DESCRIPTION OF THE INVENTION

The following definitions of various terms used throughout this specification will be used in describing the operation, objects and advantages of the present invention.

A "feed mixture" is a mixture containing one or more extract components and one or more raffinate components to be fed to an adsorbent of the process. The term "feed stream" indicates a stream of feed mixture which passes to an adsorbent used in the process.

An "extract component" is a type of compound or a compound that is more selectively adsorbed by the adsorbent while a "raffinate component" is a compound or type of compound that is less selectively adsorbed. In this process, triglycerides with less unsaturation are extract components and the more unsaturated triglycerides are raffinate components. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely nonadsorbed by the adsorbent. Therefore, small amounts of a raffinate component can appear in the extract stream, and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, in one embodiment, the ratio of the concentration of the more selectively adsorbed triglycerides to the concentration of less selectively adsorbed triglycerides will be highest in the extract stream, next highest in the feed mixture, and lowest in the raffinate stream. Likewise, the ratio of the less selectively adsorbed triglycerides to the more selectively adsorbed triglycerides will be highest in the raffinate stream, next highest in the feed mixture, and the lowest in the extract stream. The term "desorbent material" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of the desorbent material will be separated at separation conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "nonselective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the nonselective void volume are generally expressed in volumetric quantities and are of importance in determining the proper flow rates of fluid required to be passed into the process for efficient operations to take place for a given quantity of adsorbent.

The term "desorbent material" as used herein shall mean any fluid substance capable of removing a selectively adsorbed feed component from the adsorbent. Generally, in a swing-bed system in which the selectively adsorbed feed component is removed from the adsorbent by a purge stream, desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic adsorbents and which are generally operated continuously at substantially constant pressures and temperatures to ensure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, the desorbent must not react with either the adsorbent or any component of the feed material and must not reduce or destroy the critical selectivity of the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is, therefore, contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture.

In the preferred isothermal, isobaric, liquid-phase operation of the process of this invention, toluene, ketones, e.g., methylethyl ketone, methyl isobutyl ketone, diethyl ketone, acetone, mixtures of a ketone and a paraffinic hydrocarbon, e.g. hexane and isooctane, have been found to be effective desorbents.

The prior art has recognized that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressd between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases, respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or nonadsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally, desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material with the desorbent material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and, therefore, permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a nonadsorbed tracer (n-tetradecane n-$C_{14}$), for instance, and of the particular feed material all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternately, effluent samples can be collected periodically and later analyzed separately by gas or liquid chromatography.

From information derived from the chromatographic traces, adsorbent performance can be rated in terms of capacity index for an extract component, selectivity for one isomer with respect to the other, and the rate of desorption of an extract component by the desorbent.

The capacity index may be characterized by the distance between the center of the peak envelope of the selectively adsorbed isomer and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disapearance of an extract component which has just been desorbed. This distance is again the volume of desorbent pumped during this time interval.

The adsorbents to be used in the process of this invention comprise specific crystalline aluminosilicates and activated carbon or carbonized polymeric resins. Crystalline aluminosilicates such as that encompassed by the present invention include crystalline aluminosilicate cage structures in which the alumina and silica tetrahedra are intimately connected in an open three-dimensional network. The tetrahedra are crosslinked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves," although widely used, is not strictly suitable since the separation of specific triglycerides is apparently dependent on differences in electrochemical attraction of the different triglycerides and the adsorbent rather than solely on physical size differences in the triglyceride molecules.

In hydrated form, the crystalline aluminosilicates generally encompass those zeolites represented by the Formula below:

Formula 1 where "M" is a cation which balances the electrovalence of the tetrahedra and is generally referred to as an exchangeable cationic site, "n" represents the valence of the cation, "w" represents the moles of $SiO_2$, and "y" represents the moles of water. The generalized cation "M" may be monovalent, divalent or trivalent cations or mixtures thereof.

The omega type structured zeolite in the hydrated or partially hydrated form can be closely approximated in terms of mole oxides as shown in Formula 2 below (*Probable Structure of Zeolite* $\Omega$, R. M. Barrer et al., Chemical Communications, 1969, 12, pp 659–60):

Formula 2 where "TMA" is tetra methyl ammonium. The $SiO_2/Al_2O_3$ ratio for the hydrogen type omega zeolite is about 7.13.

Typically, adsorbents used in separative processes contain the crystalline material dispersed in an amorphous binder material or inorganic matrix, having channels and cavities therein which enable liquid access to the crystalline material. Also, in the case of the present invention, the adsorbent, especially omega zeolite, may be binderless. Silica, alumina, bentonite, or mixtures thereof are typical of such inorganic matrix materials. The binder aids in forming or agglomerating the crystalline particles which otherwise would comprise a fine powder. The adsorbent may thus be in the form of particles such as extrudates, aggregates, tablets, macrospheres or granules having a desired particle range, preferably from about 16 to about 60 mesh (Standard U.S. Mesh). Carbons useful in this invention include activated carbons and carbonized resins. Activated carbons can be produced from natural sources such as coal or coconut shells, while carbonized resins can be made from functionalized or unfunctionalized polymeric material. Examples of carbons useful in the present invention include Purasiv carbon, used in the Union Carbide Purasiv process, and XE 348 carbon, from Rohm and Haas.

The adsorbent may be employed in the form of a dense fixed bed which is alternately contacted with a feed mixture and a desorbent material in which case the process will be only semicontinuous. In another embodiment, a set of two or more static beds of adsorbent may be employed with appropriate valving so that a feed mixture can be passed through one or more adsorbent beds of a set while a desorbent material is passed through one or more of the other beds in a set. The flow of a feed mixture and a desorbent material may be either up or down through an adsorbent in such beds. Any of the conventional apparatus employed in a static bed fluid-solid contacting may be used.

Moving bed or simulated moving bed flow systems, however, have a much greater separation efficiency than fixed bed systems and are, therefore, preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique," by D. B. Broughton presented at the 34th Annual Meeting of the Society of Chemical Engineers at Tokyo, Japan on Apr. 2, 1969, both references incorporated herein by reference for further explanation of the simulated moving bed countercurrent process flow scheme.

Another embodiment of a simulated moving bed flow system suitable for use in the process of the present invention is the cocurrent high efficiency simulated moving bed process disclosed in U.S. Pat. No. 4,402,832 to Gerhold, incorporated by reference herein in its entirety.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at last a portion of the desorbent material can be separated at separating conditions to produce a desorbent stream which can be reused in the process and a raffinate product containing a reduced concentration of desorbent material. Typically, the concentration of desorbent material in the extract product and the raffinate product will be less than about 5 vol. % and more preferably less than about 1 vol. %. The separation means will typically be a fractionation column, the design and operation of which is well known to the separation art.

Although both liquid and vapor phase operations can be used in many adsorptive separation processes, liquid-phase operation is preferred for this process because of the high boiling points of the triglycerides. Adsorption conditions will include a temperature range of from about 20° C. to about 250° C. with about 100° C. to about 200° C. being more preferred and a pressure sufficient to maintain liquid phase. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc's an hour up to many thousands of gallons per hour.

The following examples are presented for illustration purposes and more specifically are presented to illustrate the selectivity relationships that make the process of the invention possible. Reference to specific cations, desorbent materials, feed mixtures and operating conditions is not intended to unduly restrict the scope and spirit of the claims attached hereto.

BRIEF DESCRIPTION OF THE DRAWINGS

FIGS. 1-4 are chromatographic traces of the pulse tests described in Examples II through V, illustrating the separations achieved with omega and carbon adsorbents and desorbents. Natural oils obtained from plant sources, such as safflower oil, palm oil and cocoa butter are mixtures of triglycerides. Safflower oil and cocoa butter are relatively simple mixtures. Safflower contains predominately polyunsaturated triglycerides (PUT) such as trilinolein, while cocoa butter contains mostly monounsaturated triglycerides (MUT), such as 1,3-stearyl 2-oleyl glyceride (SOS).

EXAMPLE I

A static test was made to determine the ability of two adsorbents, carbon and omega type zeolite, to separate triglycerides having a lower degree of unsaturation from triglycerides having a higher degree of unsaturation. In the test, a measured amount of adsorbent was placed in a container and a feed mixture added and allowed to stand until equilibrium was reached. The various fluids were measured to determine amount and composition of each to calculate the ratio, CF/CI, of the final concentration to the initial concentration of each component. The results are listed in Table I.

TABLE 1

|  | A | B |
| --- | --- | --- |
| Stock Solution: Triolein and Trilinolein in Isooctane | 0.059 wt. % | 0.054 wt. % |
| Initial Ratio, Triolein/Trilinolein | 1.167 | 1.065 |
| Equilibrium Ratio of Triolein to Trilinolein | 0.248 | 2.325 |
| CF/CI, Triolein | 0.008 | 0.785 |
| CF/CI, Trilinolein | 0.04 | 0.360 |
| Adsorbent | Purasiv Carbon | K-Exchanged Omega W/Attapulgite Binder |
|  | 0.47 gm/cc Stock Solution | 0.25 gm/cc Stock Solution |

In IA, triolein was selectively adsorbed. In IB, trilinolein was the selectively adsorbed component.

EXAMPLE II

In this experiment, the pulse test was performed to evaluate the ability of the present invention to separate trilinolein from triolein. The feed mixture comprised 0.2 g trilinolein, 0.2 g triolein, 0.1 g $C_{14}$ tracer, 1.5 cc hexane. The adsorbent used was a potassium-exchanged omega zeolite and can be prepared by mixing with 20 wt. % attapulgite clay. The adsorbent was redried at 600° C. before it was utilized in the process in each test.

The adsorbent so produced was used to evaluate the ability of the present invention to separate triglycerides having a higher degree of saturation from triglycerides with a higher degree of unsaturation. For this pulse test, the column was maintained at a temperature of 156° C. and a pressure of 200 psig. Liquid chromatographic analysis equipment was used to analyze the column effluent stream in order to determine the composition of the effluent material at given time intervals. The operations taking place for each test were as follows: The desorbent material was run continuously at a nominal liquid hourly space velocity (LHSV) of 1.0. The desorbent mixture was 50% toluene in hexane. At some convenient time interval, a pulse of the feed mixture was introduced. The desorbent stream was then resumed at 1 LHSV and continued to pass into the adsorbent column until all of the feed components had been eluted from the column as determined by chromatographic analysis of the effluent material leaving the adsorption column. In most cases, the column effluent is analyzed for its various triglyceride components.

Figure 1:
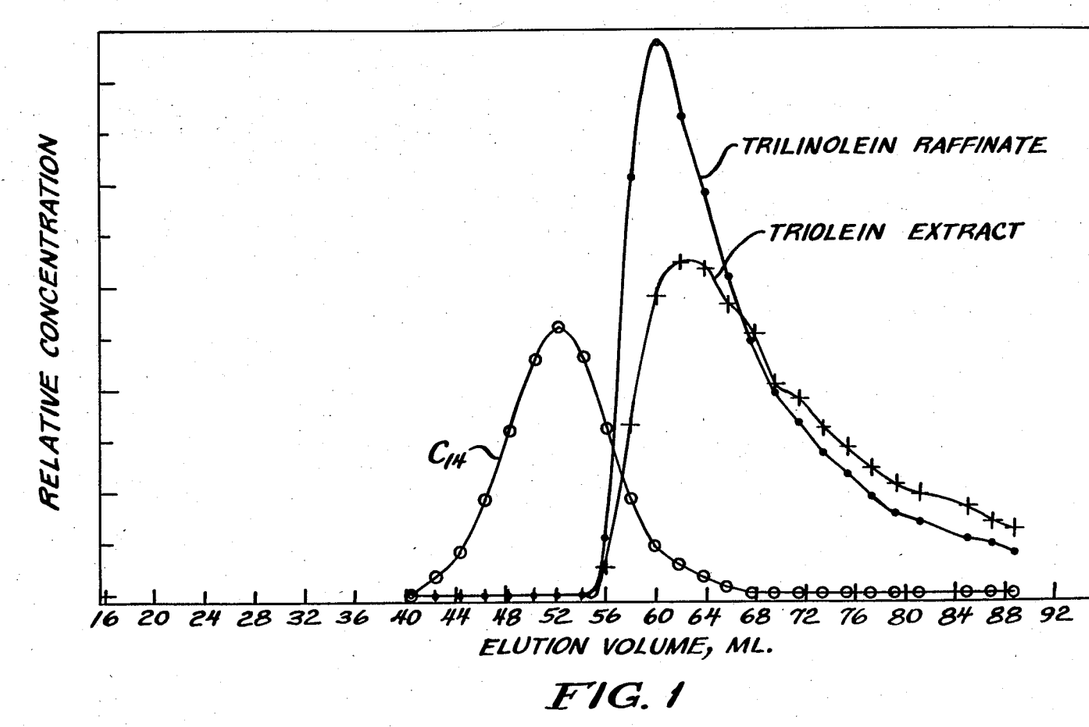

The results of the test of this Example are shown on the accompanying FIG. 1 which comprises the chromatographic trace.

It can be discerned from the test that the separation of triolein from trilinolein is readily achieved by the process of the present invention. From Equation 1, the selectivity for the trilinolein relative to the triolein is 1.39. The retention volume of trilinolein and triolein was 13.65 and 9.8 cc, respectively.

EXAMPLE III

The pulse test of Example I was repeated for omega type molecular sieves. In this test, binderless hydrogen-exchanged omega zeolite that had been dried in air at 600° C. was used. The temperature was 80° C. and the desorbent was 100 vol. % toluene. The feed was 0.5 g cocoa butter (MUT); 0.5 g safflower oil (PUT); 0.28 g n-C$_{14}$ (tetradecane); and 1.0 cc desorbent.

Figure 2:
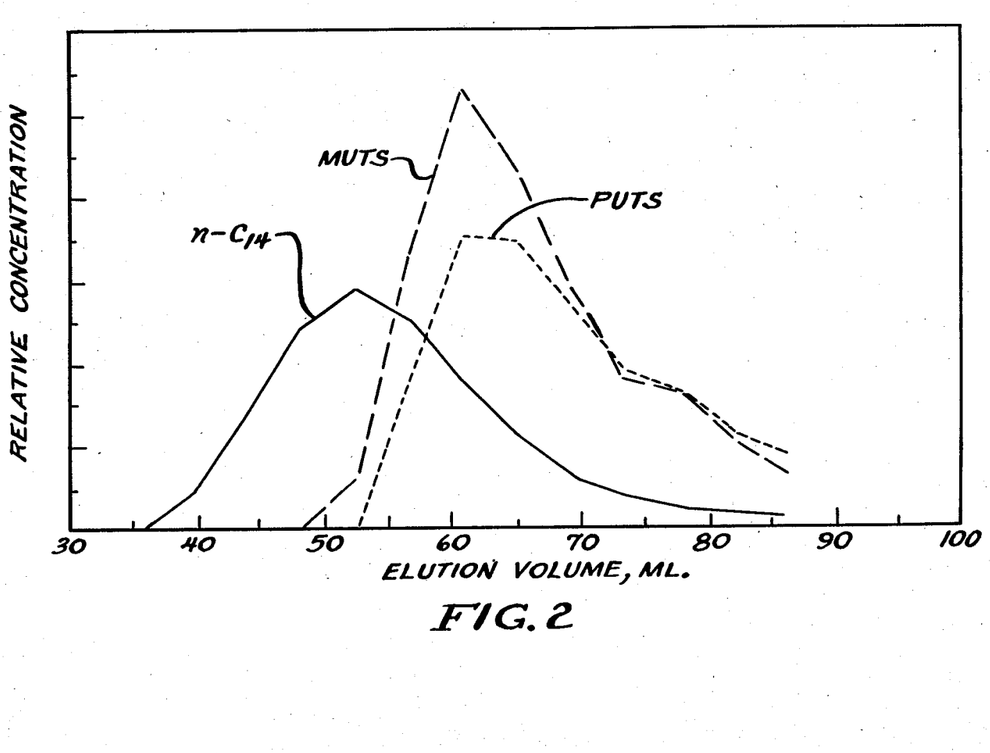

It can be seen from FIG. 2, which yields a polyunsaturated triglyceride (PUT) retention volume of 63 cc and a monounsaturated triglyceride (MUT) retention volume of 66.6 cc, that the adsorbent of the present invention exhibits acceptable selectivity B$_{PUT/MUT}$=1.38 for the polyunsaturated glycerides.

EXAMPLE IV

The following example illustrates how the present invention can be used in a two-step desorption process to obtain triglycerides which are highly enriched based on degree of unsaturation.

The pulse test of Example III was repeated except that a copper-exchanged omega zeolite with a bentonite binder was used for the adsorbent. The feed compositon was as follows: 0.5 g cocoa butter (PUT); 0.5 g safflower (MUT); 0.25 n-C$_{14}$; 1 cc desorbent.

Figure 3:
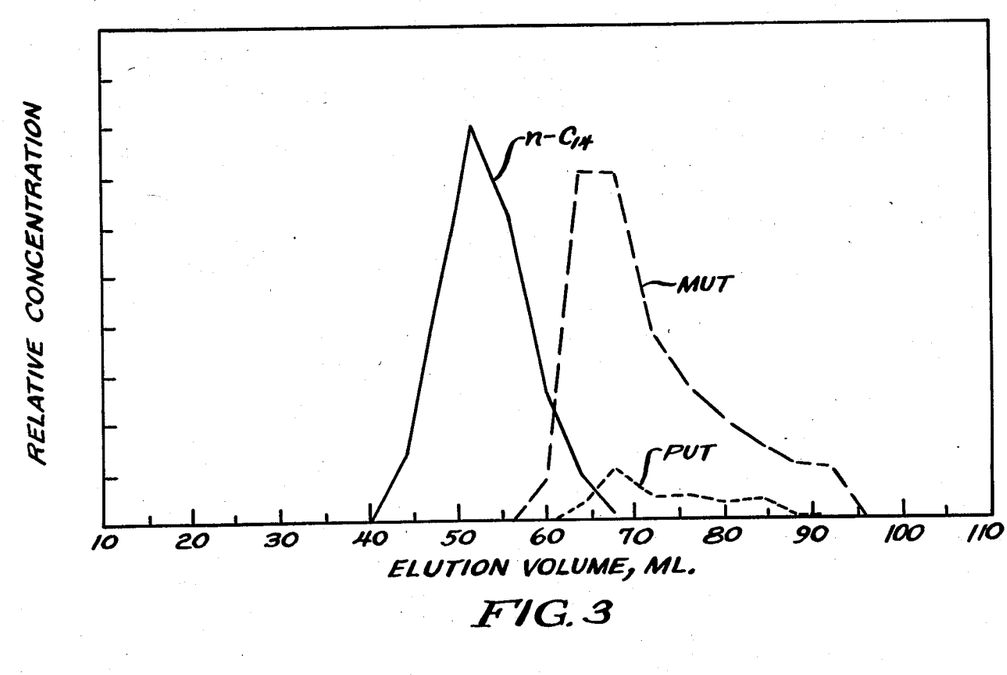

It can be seen from FIG. 3 that the monounsaturated triglycerides (MUT) are eluted from the column, whereas the polyunsaturated triglycerides (PUT) are only slightly desorbed, resulting in an extract product highly enriched in MUT.

Figure 4:
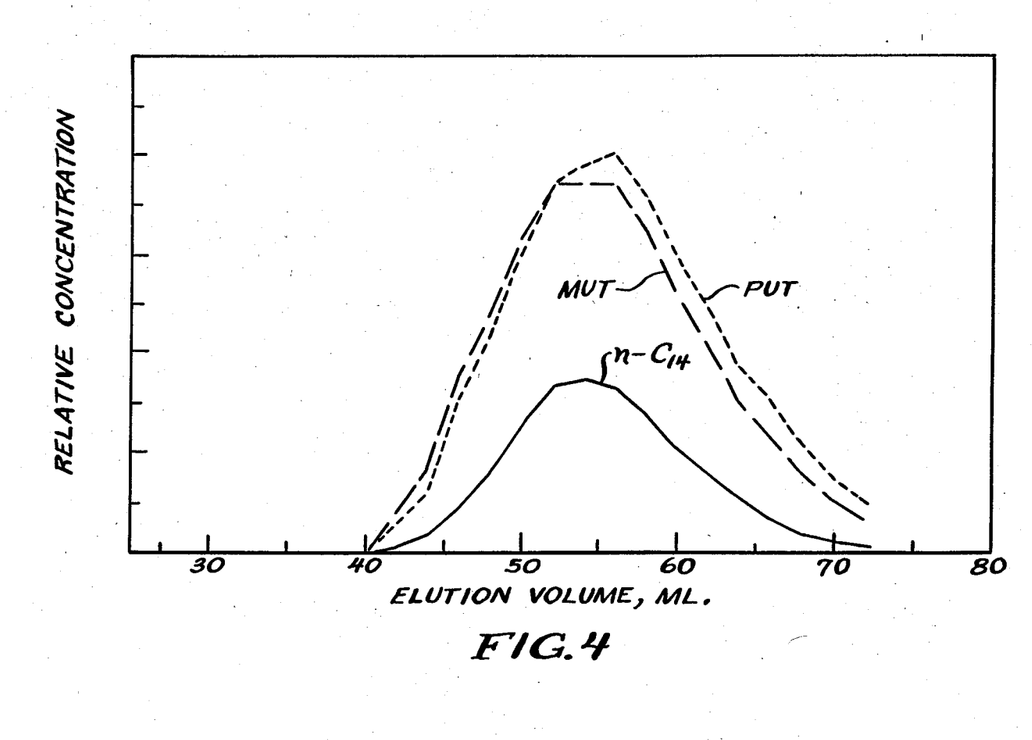

The pulse test was then repeated except that the desorbent was 20% methyl isobutyl ketone (MIBK) and 80% isooctane (i-C$_8$). From FIG. 4 it can be seen that both MUT and PUT are desorbed from the column, with selectivity for PUT. It can be seen that if, instead of a new sample, the adsorbent column from the first separation, containing Cu-omega with adsorbed polyunsaturated triglycerides (PUT) (FIG. 3), is desorbed in a second step with MIBK and i-C$_8$, the extract product will be highly enriched in polyunsaturated triglycerides (PUT) as seen in FIG. 4.

EXAMPLE V

Figure 5:
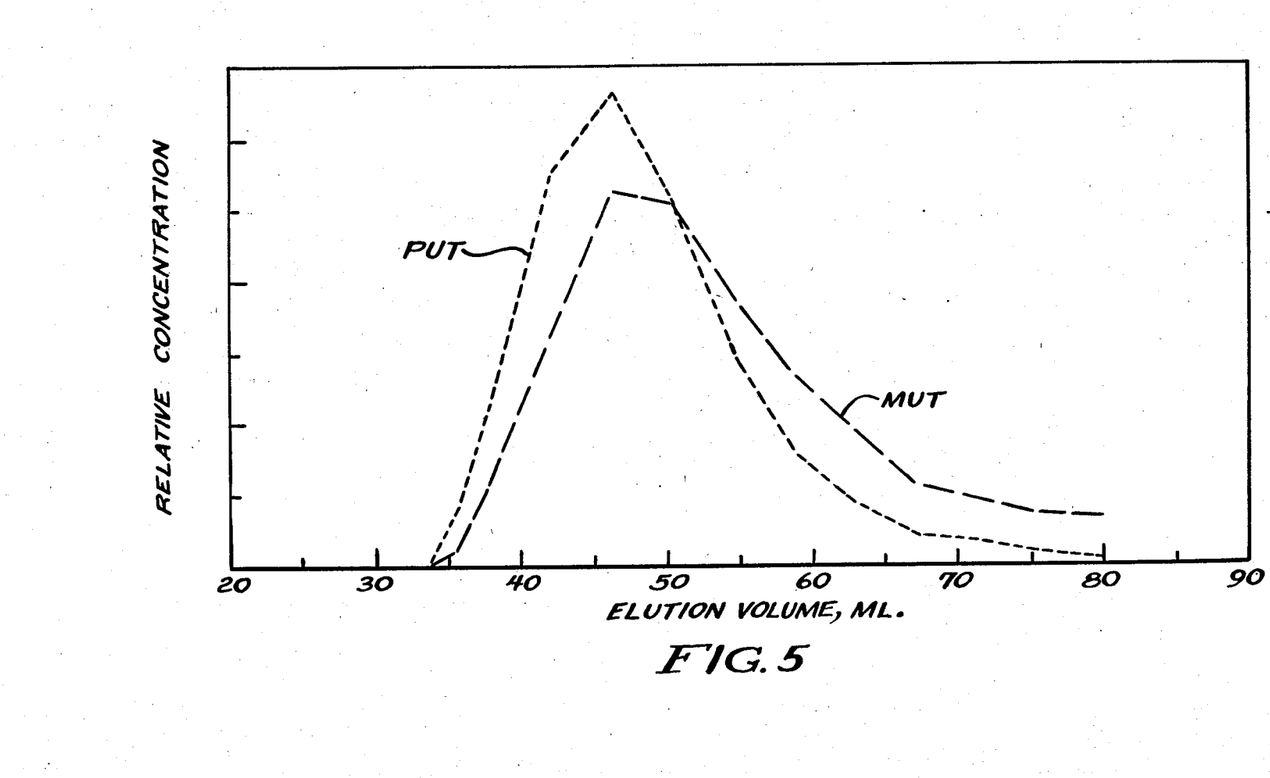

The pulse test of Example II was repeated except that XE 348 carbon was used as the adsorbent at a temperature of 60° C. From FIG. 5, it is noted that in contrast to the preceeding examples, the carbon adsorbent is selective for the monounsaturated triglycerides (MUT).

What is claimed is:

1. A process for separating triglycerides having the higher degree of unsaturation from a mixture of triglycerides having varying lower degrees of unsaturations, said process comprising contacting said mixture at adsorption conditions with an adsorbent comprising an omega-type zeolite exchanged with Cu, H or K at exchangeable sites thereby selectively absorbing said triglycerides having the higher degree of unsaturation thereon and desorbing at desorption conditions said adsorbed triglycerides with a desorbent selected from the group consisting of toluene, ketones and mixtures of ketones with paraffin hydrocarbons.

2. The process of claim 1 wherein said desorbent is selected from the group consisting of methylethyl ketone, diethyl ketone, methyl isobutyl ketone, acetone and mixtures thereof with hexane.

3. The process of claim 1 wherein said desorbent material comprises methyl isobutyl ketone.

4. The process of claim 2 wherein said desorbent material is toluene.

5. The process of claim 1 wherein said adsorption conditions include a temperature within the range of from about 20° C. to about 200° C. and a pressure sufficient to maintain liquid phase.

6. The process of claim 1 wherein said more highly unsaturated triglyceride is polyunsaturated trilinolein and said less highly unsaturated triglyceride is triolein.

7. A process for separating a triglyceride having a higher degree of unsaturation from a feed mixture comprising triglyceride having varying degrees of unsaturation, which process employs an adsorbent selected from the group consisting of an omega zeolite exchanged with Cu, H or K at exchangeable cationic sites which process comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said aosorption zone, said purification zone defined by the adsorbent located between an extract output stream at an upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed mixture into said adsorption zone at adsorption conditions to effect the selective adsorption of said triglyceride by said adsorbent in said adsorption zone and withdrawing a raffinate output stream from said adsorption zone;

(f) passing a desorbent material comprising toluene, methyethyl ketone, methylisobutyl ketone, acetone or diethyl ketone into said desorption zone at desorption conditions to effect the displacement of said triglyceride from the adsorbent in said desorption zone;

(g) withdrawing an extract output stream comprising said triglyceride and desorbent material from said desorption zone;

(h) withdrawing a raffinate output stream comprising said triglyceride from said desorption zone; and (i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output stream.

8. The process of claim 7 wherein said adsorption and desorption conditions include a temperature within the range of from about 20° C. to about 200° C. and a pressure sufficient to maintain liquid phase.

9. The process of claim 7 wherein a buffer zone is maintained immediately upstream from said desorption zone, said buffer zone is defined as the adsorbent located between the desorbent input stream as the downstream boundary of said buffer zone and the raffinate output stream at an upstream boundary of said buffer zone.

10. A process for separating triglycerides having the lower degree of unsaturation from a mixture of triglycerides having varying degrees of unsaturation, said process comprising contacting said mixture at adsorption conditions with an adsorbent comprising carbon thereby selectively adsorbing said triglycerides having the lower degree of unsaturation and desorbing at desorption conditions said adsorbed triglycerides with a desorbent selected from the group consisting of toluene, ketones and mixtures of ketones with paraffin hydrocarbons.

11. The process of claim 10 wherein said desorbent is toluene.

12. The process of claim 10 wherein said adsorption conditions include a temperature within the range of from about 20° C. to about 200° C. and a pressure sufficient to maintain a liquid phase.

13. A process for separating triglycerides having a higher degree of unsaturation from a mixture of triglycerides having varying lower degrees of unsaturations including monounsaturated triglycerides, said process comprising contacting said mixture at adsorption conditions with an adsorbent comprising copper-exchanged omega zeolite thereby selectively absoring said triglycerides having the higher degree of unsaturation thereon and desorbing in a first desorption step at desorption conditions said triglycerides with lower degree of unsaturation with a desorbent consisting of toluene thereby obtaining triglycerides enriched in less unsaturated triglycerides, desorbing in a second desorption step at desorption conditions, said triglycerides having high degree of unsaturation with a desorbent selected from the group consisting of ketones and mixtures of ketones with paraffin hydrocarbons.

14. The process of claim 13 wherein the second desorbent comprises methyl isobutyl ketone.

15. The process of claim 14 wherein the second desorbent additionally comprises isooctane.

16. A process for separating triglycerides having varying lower degrees of unsaturation from a mixture of triglycerides having varying degrees of unsaturation, said process comprising contacting said mixture at adsorption conditions with an adsorbent comprising carbon, thereby selectively adsorbing said triglycerides having lower degrees of unsaturation thereon and desorbing said adsorbed triglycerides at desorption conditions with a desorbent comprising toluene.

17. The process of claim 16 wherein said triglycerides having lower degrees of unsaturation comprise monounsaturated triglycerides.

* * * * *